United States Patent
Calleri

(10) Patent No.: US 10,962,464 B2
(45) Date of Patent: Mar. 30, 2021

(54) METHOD FOR DETERMINING AN EXTRACTION EFFICIENCY OF AT LEAST ONE VOLATILE SPECIES CONTAINED IN A DRILLING MUD

(71) Applicant: GEOLOG S.R.L., San Giuliano Milanese (IT)

(72) Inventor: Antonio Calleri, Milan (IT)

(73) Assignee: Geolog S.R.L., San Giuliano Milanese (IT)

( * ) Notice: Subject to any disclaimer, the term of this patent is extended or adjusted under 35 U.S.C. 154(b) by 295 days.

(21) Appl. No.: 16/113,610

(22) Filed: Aug. 27, 2018

(65) Prior Publication Data
US 2019/0072475 A1 Mar. 7, 2019

(30) Foreign Application Priority Data
Sep. 1, 2017 (IT) .................. 102017000098502

(51) Int. Cl.
*E21B 21/06* (2006.01)
*G01N 15/08* (2006.01)
(Continued)

(52) U.S. Cl.
CPC ......... *G01N 15/082* (2013.01); *E21B 21/067* (2013.01); *E21B 49/086* (2013.01); *G01N 33/2823* (2013.01); *G01N 1/44* (2013.01)

(58) Field of Classification Search
CPC .... G01N 15/082; G01N 33/2823; G01N 1/44; E21B 49/086; E21B 21/067
See application file for complete search history.

(56) References Cited

U.S. PATENT DOCUMENTS

2006/0224333 A1   10/2006   Frechin et al.
2009/0050369 A1*   2/2009   Pop ..................... E21B 49/081
                                                                   175/42
(Continued)

FOREIGN PATENT DOCUMENTS

EP   3 182 119 A1   6/2017
WO   2014/137356 A1   9/2014
WO   2015/076839 A1   5/2015

OTHER PUBLICATIONS

Italian Search Report dated Apr. 25, 2018, issued in Italian Application No. IT201700098502.

*Primary Examiner* — Suman K Nath
(74) *Attorney, Agent, or Firm* — Workman Nydegger

(57) ABSTRACT

Method for determining an extraction efficiency of at least one volatile species contained in a drilling mud, the method including: housing a test mud in a first closed container; determining a test parameter representative of a ratio between a first portion of at least one first volatile species, which is absorbed by the test mud, and a second portion of the first volatile species, which is not absorbed by the test mud, the second portion of the first volatile species being measured in a headspace of the first closed container; housing a drilling mud in a second closed container, the drilling mud containing at least one second volatile species, the second volatile species being substantially the same as the first volatile species; determining an operating parameter representative of a quantity of the second volatile species released by the drilling mud in the second closed container, wherein the quantity of the second volatile species is measured in a headspace of the second closed container; determining, as a function of the operating parameter and the test parameter, an absorption parameter indicative of a quantity of the second volatile species in the drilling mud; determining, as a function of the absorption parameter, an extraction (Continued)

efficiency of the second volatile species from the drilling mud.

21 Claims, 3 Drawing Sheets

(51) Int. Cl.
*G01N 33/28* (2006.01)
*E21B 49/08* (2006.01)
*G01N 1/44* (2006.01)

(56) References Cited

U.S. PATENT DOCUMENTS

| | | |
|---|---|---|
| 2010/0089120 A1 | 4/2010 | Hanson |
| 2017/0167257 A1 | 6/2017 | Rowe |
| 2018/0334606 A1* | 11/2018 | Scalley ................. E21B 21/068 |

* cited by examiner

METHOD FOR DETERMINING AN EXTRACTION EFFICIENCY OF AT LEAST ONE VOLATILE SPECIES CONTAINED IN A DRILLING MUD

CROSS-REFERENCE TO RELATED APPLICATIONS

This application claims priority to Italian Application No. 102017000098502, filed Sep. 1, 2017, which is incorporated herein by specific reference.

BACKGROUND OF INVENTION

Technical Field

The present invention relates to a method for determining an extraction efficiency of at least one volatile species contained in a drilling mud.

Prior Art

The technical field to which the present invention refers is the exploration and exploitation of the petroliferous and geothermal resources in the subsoil.

When drilling a well for hydrocarbon extraction, a fluid called drilling mud is made to circulate within the wellbore.

Drilling mud use is aimed at lubricating and cooling the drilling bit, as well as maintaining an adequate hydrostatic pressure inside the well.

The drilling mud is fed into the hollow interior of the drilling line and goes back up in the annular space delimited by the outer surface of the drilling bit and the inner surface of the well. After having reached the surface, the returning mud flows along a return line, also referred to as flow line, at the end of which the solid debris dragged by the mud are separated from the fluidic component.

The fluidic component is then fed back into the tank in which it was before circulating in the well, so that it can be reused.

As it flows through the flow line, a part of the fluidic component is withdrawn by means of a pump, associated with a suitable filter, and fed to a degasser, wherein the gas dissolved in the mud is extracted.

The volatile components extracted by the degasser are then subjected to analysis for the purpose of obtaining information about the characteristics of any hydrocarbon resources and, more generally, of any gases that may be present in the subsoil.

The state of the art provides also solutions wherein the fluidic component coming from the well is not withdrawn from the flow line: the gaseous components dissolved in the mud are extracted directly in the flow line. To this end, probes are used which are equipped with semi-permeable membranes allowing only certain molecules to pass by diffusion. The gases thus extracted can then be examined, e.g., by means of chromatographic analysis procedures.

Document US 2010/0089120 describes a method for characterizing the fluids present in a subsoil formation during drilling, which uses systems for correcting the measured concentrations of gaseous components in the drilling mud. Values for the gas components of interest, light hydrocarbons, are measured during mud logging and are corrected using relative response factors, determined from laboratory analyses and relative extraction efficiency values.

Document US 2017/0167257 A1 describes methods for determining the gas extraction efficiency from a drilling fluid. Such methods may comprise: combining a measured amount of an analysis gas with a drilling fluid sample; transferring the drilling fluid sample and the analysis gas to a degassing unit; withdrawing at least a portion of the analysis gas from the drilling fluid sample in the degassing unit; conveying the withdrawn analysis gas from the degassing unit to a detector with an inert carrier gas; determining an amount of the withdrawn gas with the detector; calculating an extraction efficiency of the analysis gas from the drilling fluid sample based upon the amount of the withdrawn analysis gas.

Document US 2006/0224333 discloses a method comprising the phases of: measuring the quantity of given gas in the gases extracted from a calibration sample of a calibration mud, in at least two stages for extraction under predetermined conditions; establishing a family of curves representing the extraction, under the predetermined conditions, of the given gas from the drilling mud, on the basis of the measurements carried out. The method also includes the phases of: measuring the quantity of given gas in the gases extracted from an analysis sample of the drilling mud in an extraction stage, under the predetermined conditions; computing the given gas content of the drilling mud on the basis of the measured quantity of given gas and of a curve of said family. It has to be noted that the method disclosed in US 2006/0224333 always begins based on drilling mud samples that come from the well and initially contain a quantity of gas which is unknown. Furthermore, in order to properly apply such method, two extraction steps, in determined conditions, have to be carries out.

The Applicant has verified that the currently known methods suffer from some drawbacks, which are mainly related to the complexity of the procedure and to the limited reliability and accuracy of the obtained results.

OBJECTS AND SUMMARY OF THE INVENTION

It is one object of the present invention to provide a method for determining an extraction efficiency of a volatile species contained in a drilling mud, which is both accurate and reliable.

It is another object of the invention to provide a method for determining an extraction efficiency of a volatile species contained in a drilling mud, which can be carried out in a simple and rapid manner.

These and other objects are substantially achieved through a method for determining an extraction efficiency of a volatile species contained in a drilling mud as set out in the appended claims.

BRIEF DESCRIPTION OF THE DRAWINGS

Further features and advantages will become more apparent from the following detailed description of some preferred but non-limiting embodiments of the invention.

This description will refer to the annexed drawings, which are also provided merely as explanatory and non-limiting examples, wherein.

DETAILED DESCRIPTION OF THE INVENTION

Figure 1:
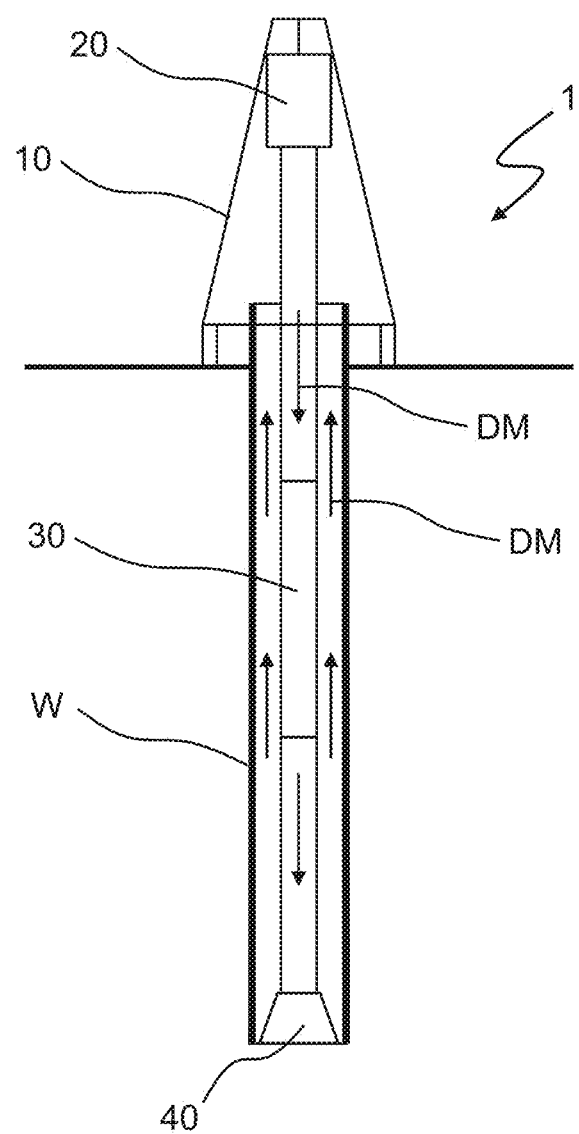
FIG. 1 schematically shows a system in which the method according to the invention can be used.

With reference to the annexed drawings, 1 designates as a whole a system in which the method according to the present invention can be used.

The system 1 is used for drilling a well W to be used for subsoil exploration and/or hydrocarbon extraction.

The system 1 comprises a support structure 10 and a motor 20 mounted on said support structure. In particular, the motor 20 may be constrained to the support structure 10 by means of a hook that allows it to translate along a substantially vertical axis. The rotary motion generated by the motor 20 is transferred to a drilling bit 40 through a pipe structure 30. The pipes 30 consist of tubular sections with threaded ends which, when assembled according to a pre-defined longitudinal development, allow the drilling bit 40 to reach depths of a few thousands of metres, while turning about their own longitudinal axis.

The assembly consisting of the pipes 30 and the drilling bit 40 will be referred to hereinafter and in the appended claims as "drilling equipment".

In order to perform the drilling operation, drilling mud DM is supplied to the drilling equipment and reaches the drilling bit 40, since it is pumped within said pipes 30. The mud, after having reached the terminal part of the drilling bit 40 at a certain pressure, goes back up through the well W, returning to the top opening located at the support structure 10.

In FIG. 1, the downward arrows on the pipes 30 represent the flow of drilling mud DM supplied to the drilling bit 40, while the upward arrows outside the pipes represent the flow of drilling mud DM returning to the surface.

Note that FIG. 1 represents the above-described elements in a schematic manner, without necessarily observing the actual proportions between the dimensions of such elements.

The drilling mud DM may consist of, for example, a base (water or oil), clays and chemical additives. Prior to being fed into the well W, the drilling mud DM contains substantially no hydrocarbon dissolved or trapped therein. Following interaction with the rocky formations that are present in the subsoil, the drilling mud DM may absorb, as it goes back up, variable quantities of volatile species, e.g., hydrocarbons, depending on the type of volatile species and the characteristics of the rocky formation it has flowed through. Determining such quantities may allow deriving interesting information about the subsoil and any reservoir. As will become more apparent below, the method according to the invention is aimed at calculating the extraction efficiency of volatile species in the drilling mud DM after the latter has flowed back up the well.

Extraction efficiency is representative of the ratio between the quantity of a volatile species extracted from the drilling mud and the quantity of the same volatile species that was initially present in the drilling mud.

In accordance with the invention, a test mud TM is first provided, which can be used in a subsoil drilling system such as, for example, the system schematized in FIG. 1.

The test mud TM has substantially the same characteristics as the drilling mud DM which is actually used for drilling, e.g., to be fed to said drilling equipment.

This means that, the chemical, physical and mechanical conditions being equal, the test mud TM and the drilling mud DM behave in the same way in terms of capability of absorbing and/or trapping volatile species, e.g., hydrocarbons.

By way of example, the test mud TM may be a sample taken from the very same drilling mud DM before the latter is fed to the drilling equipment.

In a different embodiment of the invention, the test mud TM may not be exactly the same as that which will subsequently be used for drilling, but a mud that, as aforesaid, has substantially the same characteristics as the drilling mud DM.

Preferably, the test mud TM is substantially free from the volatile species for which extraction efficiency needs to be calculated. For example, the test mud may be substantially free from hydrocarbons.

Figure 2A:
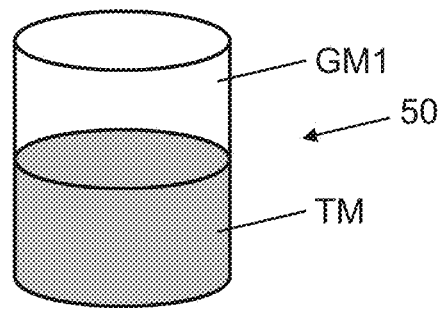
FIGS. 2a-2d and 3a-3b schematically show steps included in an embodiment of the method according to the invention.

A quantity of test mud TM is housed in a first closed container 50 (FIG. 2*a*).

Preferably, the first closed container 50 is hermetically closed.

The first closed container 50 is thus occupied partly by test mud TM and partly by a first gaseous mixture GM1.

As schematized in FIG. 2*a*, the test mud TM occupies the lower part of the first closed container 50, also referred to as bottom space, and the first gaseous mixture GM1 occupies the upper part of the first closed container 50, also referred to as headspace.

The first gaseous mixture GM1 is preferably free from the volatile species for which extraction efficiency needs to be calculated. For example, the first gaseous mixture GM1 is substantially free from hydrocarbons.

In practice, the first gaseous mixture GM1 may substantially consist of air that is present in the environment where the first container 50 is located prior to being closed.

The first gaseous mixture GM1 in the first closed container 50 is at an initial pressure.

Figure 2B:
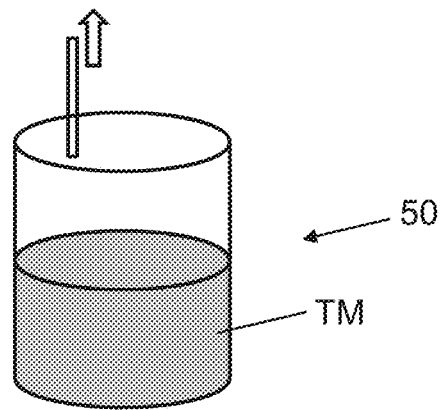

Preferably, at least a part of the first gaseous mixture GM1 is extracted from the first closed container 50 (FIG. 2*b*).

This extraction step can be carried out, for example, by means of a syringe-like device suitable for aspirating the first gaseous mixture GM1, possibly with the aid of one or more valves, so as to maintain the separation between the inside and the outside of the first closed container 50.

The at least partial removal of the first gaseous mixture GM1 causes a depressurization within the first closed container 50.

Note that the first gaseous mixture GM1 may be removed either completely or only partially. As will become more apparent below, the purpose of this extraction is to make room for a second gaseous mixture GM2, which may not require the complete removal of the first gaseous mixture GM1.

Figure 2C:
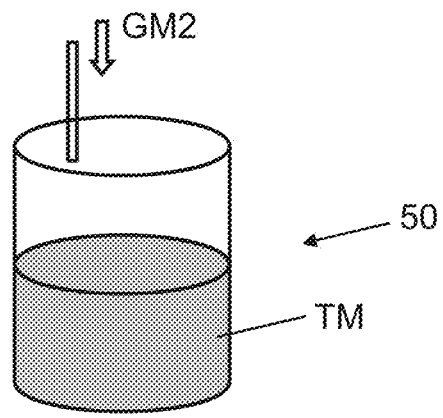

The second gaseous mixture GM2 is introduced into the first closed container 50 in order to re-establish said initial pressure (FIG. 2*c*).

The fact that the initial pressure has been re-established can be verified by means of a suitable probe (not shown), associated with the first closed container 50, through which the pressure is measured before extracting the first gaseous mixture GM1 and after introducing the second gaseous mixture GM2.

Preferably, in order to introduce the second gaseous mixture GM2 into the first closed container 50, one can employ the same device as that already used for removing the first gaseous mixture GM1.

The second gaseous mixture GM2 comprises at least a known quantity one first volatile species, e.g., a hydrocarbon gas. Such hydrocarbon gas may belong to, for example, the C1-C5 group or the C6-C8 group.

Preferably, the test mud TM is heated up to a predefined temperature. Such temperature may be comprised, for example, between 40° C. and 90° C.

Preferably, the test mud TM is heated up before the introduction of the second gaseous mixture GM2 into the first closed container 50.

In one embodiment, the test mud TM is heated up before and/or during the (at least partial) removal of the first gaseous mixture GM1.

In one embodiment, the test mud TM is heated up also after the second gaseous mixture GM2 has been introduced into the first closed container 50.

In accordance with the invention, a step is carried out in order to determine a test parameter representative of a ratio between a first portion of the first volatile species, which is absorbed by the test mud TM, and a second portion of the first volatile species, which is not absorbed by the test mud TM.

In other words, the quantity of the first volatile species introduced into the first closed container 50 being known, it is determined how much of it is absorbed by the mud and how much of it remains free within the first closed container 50.

The second portion of the first volatile species is measured in the headspace of the first closed container 50.

Preferably, after having introduced the second gaseous mixture GM2 into the first closed container 50, one waits for said test mud TM and the second gaseous mixture GM2 to reach a substantial kinetic equilibrium before determining said test parameter.

By way of example, the waiting time of this step may be approx. 1-1.5 h.

Figure 2D:
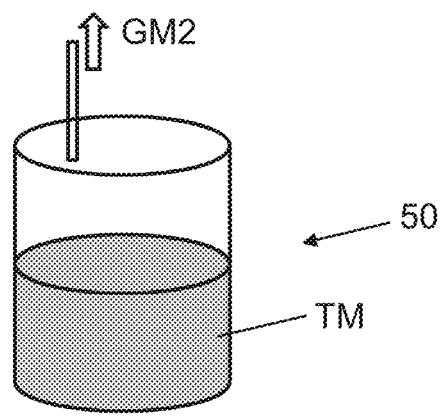

In order to determine the test parameter, at least a part of said first volatile species is extracted from the first closed container 50, in particular from the headspace thereof (FIG. 2d).

By way of example, for this extraction step one may use the same device as that already used for removing, at least partly, the first gaseous mixture GM1 and/or for introducing the second gaseous mixture GM2.

Based on said first volatile species extracted, a first value is determined, which is indicative of the total quantity of the first volatile species that has not been absorbed by the test mud TM; in other words, it is determined how much of the first volatile species has remained free in the first closed container 50.

In one embodiment, a given volume of the gaseous mixture present in the first closed container 50 is extracted, and the concentration of the first volatile species is measured. Starting from such concentration, and measuring the total volume of the headspace, it is possible to calculate said first value.

As a function of the first value, which is indicative of the total quantity of the first volatile species that has not been absorbed by said test mud TM, a second value is calculated, which is indicative of a total quantity of the first volatile species that has been absorbed by the test mud TM.

In one embodiment, the second value can be calculated as the difference between the (known) total quantity of the first volatile species introduced into the first closed container 50 and the calculated first value.

Once the first and second values have been determined, the test parameter can be calculated, for example, as the ratio between said first and second values.

In brief, the test mud TM provides a measurement, in conditions of substantial kinetic equilibrium, of the extent to which a given total quantity of the first volatile species is divided between a portion contained/absorbed in the mud and a portion that has remained free in the gaseous phase.

Preferably, the test mud TM is subjected to a mixing step (also referred to as stirring step). Advantageously, the test mud TM is mixed before determining the test parameter, and in particular before the first volatile species is extracted (at least partly) from the first closed container 50. In a preferred embodiment, heating and stirring are preferably carried out at the same time.

Once said test parameter has been obtained, it is possible to apply the result to a drilling mud DM actually coming from a well such as, for example, the well W schematically shown in FIG. 1.

As aforesaid, the drilling mud DM has, before being used in the drilling well, substantially the same characteristics as the test mud TM. This means that, the chemical, physical and mechanical conditions being equal, the test mud TM and the drilling mud DM behave in the same way in terms of capability of absorbing and/or trapping volatile species, e.g., hydrocarbons.

Figure 3A:
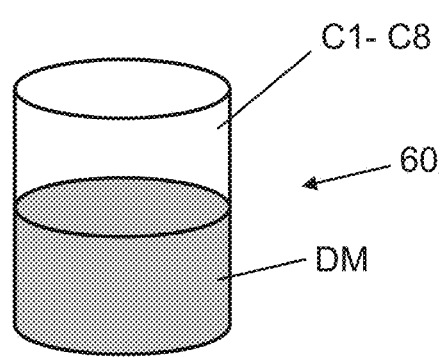

A quantity of drilling mud DM coming from the well is housed in a second closed container 60 (FIG. 3a).

For example, the second closed container 60 may be a constant-volume degasser (CVD).

Since it comes from the drilling well, the drilling mud DM has interacted with the subsoil and therefore with rocky formations containing, for example, hydrocarbons. Thus, the drilling mud DM contains an unknown quantity of volatile species, which must be determined. This step is carried out by utilizing the previously calculated test parameter.

With reference to the drilling mud DM, an operating parameter is therefore determined, which is representative of a quantity of a second volatile species released by the drilling mud DM in the second closed container 60.

Figure 3B:
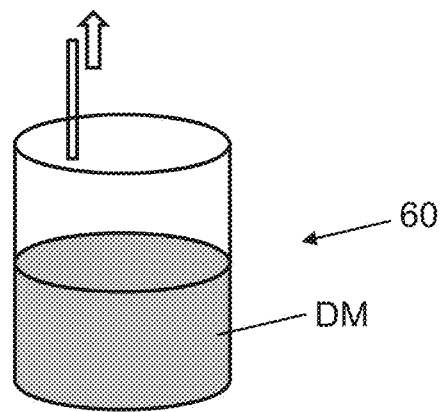

In practice, the quantity of the second volatile species released by the mud in the headspace, i.e., the upper portion, of the second closed container 60 is measured (FIG. 3b).

The second volatile species is substantially the same as the first volatile species. This means that they have substantially the same chemical formulation. For example, the first and second volatile species may consist of the same hydrocarbon.

Preferably, the method according to the invention includes a step of heating up the drilling mud DM.

In particular, the drilling mud DM is heated up prior to determining the operating parameter. More in detail, the drilling mud DM is heated up at least before the extraction, from the second closed container 60, of the quantity of the second volatile species necessary for determining the operating parameter.

Preferably, the drilling mud DM is heated up to a predefined temperature. Such temperature may be comprised, for example, between 40° C. and 90° C.

Preferably, the method according to the invention includes a step of mixing the drilling mud DM. This step is also referred to as stirring the drilling mud DM.

In particular, the drilling mud DM is mixed before determining the operating parameter. In a preferred embodiment, heating and stirring are preferably carried out at the same time.

In general, the steps of heating and stirring the test mud TM and the drilling mud DM pursue the aim of bringing both muds TM, DM into the same operating conditions, so that the measurements taken on the test mud TM can then be applied to the drilling mud DM.

As a function of said operating parameter and said test parameter, an absorption parameter is then calculated, which is indicative of a quantity of the second volatile species contained in the drilling mud DM. In particular, the absorption parameter may be indicative of the quantity of the second volatile species contained in the drilling mud DM in the second closed container 60.

Advantageously, the extraction efficiency of the second volatile species from the drilling mud DM is calculated as a function of the absorption parameter.

In particular, a value is obtained as a function of the absorption parameter and the operating parameter which is representative of the total quantity of the second volatile species that is present in the drilling mud DM before it is introduced into the second closed container 60. The ratio between the operating parameter and said total quantity represents the extraction efficiency of the second volatile species from the drilling mud DM.

As aforementioned, this datum can be used for obtaining useful information about the rocky formation or reservoir through which the drilling mud DM flows while going back up.

In summary, the above-described processing can be represented by the following equations:

$$V2 = Vtot - V1$$
$$TP = \frac{V2}{V1}$$
$$A = OP * TP$$
$$Q = A + OP$$
$$\text{eff} = \frac{OP}{Q}$$

where:

V1 is said first value, indicative of the total quantity of the first volatile species that has not been absorbed by the test mud TM, i.e., that is still free in the first closed container 50;

V2 is said second value, indicative of the total quantity of the first volatile species that has been absorbed by the test mud TM;

Vtot is the total quantity of the first volatile species introduced into the first closed container 50;

TP is the test parameter, obtained as the ratio between the second value and the first value;

OP is said operating parameter, representative of the quantity of the second volatile species released by the drilling mud DM in the second closed container 60;

A is the absorption parameter, representative of the quantity of the second volatile species that has remained in the drilling mud DM in the second closed container 60, and is calculated by multiplying the test parameter by the operating parameter;

Q is the total quantity of hydrocarbon gas that is present in the drilling mud DM before the drilling mud DM is housed in the second closed container 60;

eff is the extraction coefficient, calculated as the ratio between the operating parameter (second volatile species extracted from the drilling mud DM) and the total quantity represented by the parameter Q.

Note that the above description assumes the presence of only one volatile species in the second gaseous mixture GM2.

However, in other embodiments of the invention a plurality of volatile species may be present in the second gaseous mixture GM2.

For example, the second gaseous mixture may comprise a plurality of hydrocarbons.

In one embodiment, the second gaseous mixture GM2 may comprise C1-C5 hydrocarbons, i.e., hydrocarbons the molecule of which has 1, 2, 3, 4 and 5 carbon atoms.

In one embodiment, the second gaseous mixture GM2 may comprise C6-C8 hydrocarbons, i.e., hydrocarbons the molecule of which has 6, 7 and 8 carbon atoms.

For each volatile species in the second gaseous mixture GM2, a test parameter is determined in accordance with the above description.

Note that the volatile species are not extracted separately, one at a time, from the first closed container 50. From a practical viewpoint, at least a part of the second gaseous mixture GM2 is extracted, and then the quantity of each volatile species contained therein is verified. In this manner it is possible to calculate the test parameter for each volatile species.

Preferably, for each volatile species in the second gaseous mixture GM2, a respective operating parameter is determined.

As aforesaid with reference to the first closed container 50, the volatile species cannot be extracted separately from the second closed container 60. In this case as well, at least a part of the gaseous mixture in the second closed container 60 is extracted, and then the quantity of each volatile species contained in such gaseous mixture is determined, so as to calculate an operating parameter for each volatile species.

For each volatile species taken into account, a respective absorption parameter is then calculated and, as a function of the latter, the extraction efficiency concerning that volatile species is determined.

The invention achieves important advantages.

First and foremost, the method according to the invention allows attaining accurate and reliable results.

Furthermore, the method according to the invention can be carried out in quasi-real time, and the results are therefore available in a very short time.

In addition to the above, the tools necessary for implementing the method are very simple and inexpensive.

The invention claimed is:

1. A method for determining an extraction efficiency of at least one volatile species contained in a drilling mud, said method comprising:
    a) housing a test mud in a first closed container, said test mud being substantially free from said first volatile species;
    b) adding in said first closed container a known quantity of said first volatile species;
    c) determining a test parameter representative of a ratio between a first portion of said first volatile species, which is absorbed by said test mud, and a second portion of said first volatile species, which is not absorbed by said test mud, the second portion of said first volatile species being measured in a headspace of said first closed container;
    d) housing a drilling mud in a second closed container, said drilling mud containing at least one second volatile species, said second volatile species being substantially the same as said first volatile species;
    e) determining an operating parameter representative of a quantity of said second volatile species released by said drilling mud in said second closed container, wherein said quantity of said second volatile species is measured in a headspace of said second closed container;
    f) determining, as a function of said operating parameter and said test parameter, an absorption parameter indicative of a quantity of said second volatile species in said drilling mud;
    g) determining, as a function of said absorption parameter, an extraction efficiency of said second volatile species from said drilling mud.

2. The method according to claim 1, wherein said drilling mud comes from a drilling well and has, before being used in said drilling well, substantially the same characteristics as said test mud.

3. The method according to claim 1, wherein said test mud is housed in said first closed container in such a way that a bottom space of said first closed container is occupied by said test mud and said headspace is at least partly occupied by the second portion of said first volatile species.

4. The method according to claim 3, wherein, before being occupied by the second portion of said first volatile species, the headspace of said first closed container is occupied by a first gaseous mixture.

5. The method according to claim 4, comprising:
a) extracting at least a part of said first gaseous mixture from said first closed container;
b) introducing a second gaseous mixture containing at least said known quantity of said first volatile species into said first closed container.

6. The method according to claim 4, wherein said first gaseous mixture is substantially free from said first volatile species.

7. The method according to claim 5, wherein:
a) said first gaseous mixture in said first closed container is at an initial pressure;
b) said second gaseous mixture is introduced into said first closed container in order to re-establish said initial pressure.

8. The method according to claim 5, wherein said test mud is heated up at least before the introduction of said second gaseous mixture into said first closed container.

9. The method according to claim 4-5, wherein, after the step of introducing said second gaseous mixture into said first closed container and before the step of determining said test parameter, a step is carried out of waiting for said test mud and said second gaseous mixture to reach a substantial kinetic equilibrium.

10. The method according to claim 5, wherein said second gaseous mixture comprises a plurality of volatile species, wherein the steps of determining said test parameter, said operating parameter, said absorption parameter and said extraction efficiency are carried out for each one of said volatile species.

11. The method according to claim 1, comprising a step of heating up said test mud.

12. The method according to claim 1, comprising a step of heating up said drilling mud.

13. The method according to claim 12, wherein said drilling mud is heated up before determining said operating parameter.

14. The method according to claim 1, comprising a step of stirring said test mud.

15. The method according to claim 14, wherein said test mud is stirred before determining said operating parameter.

16. The method according to claim 1, comprising a step of stirred said drilling mud.

17. The method according to claim 16, wherein said drilling mud is stirred before determining said operating parameter.

18. The method according to claim 1, wherein said second closed container is a constant-volume degasser.

19. The method according to claim 1, wherein said test mud is said drilling mud before it is used in said drilling well.

20. The method according to claim 1, wherein the step of determining said test parameter comprises the following sub-steps:
extracting at least a part of said first volatile species from said first closed container;
determining, based on the first volatile species extracted in the previous sub-step, a first value indicative of a total quantity of the first volatile species that has not been absorbed by said test mud;
determining, based on said first value, a second value indicative of a total quantity of said first volatile species that has been absorbed by said test mud;
determining said test parameter as a function of said first value and said second value.

21. The method according to claim 1, wherein the first volatile species comprise a hydrocarbon.

* * * * *